United States Patent [19]

Broger et al.

[11] 4,283,559
[45] Aug. 11, 1981

[54] PROCESS FOR THE MANUFACTURE OF CYCLOHEXENE DERIVATIVES

[75] Inventors: Emil A. Broger, Magden; Yvo Crameri, Oberwil; Hans G. W. Leuenberger, Bättwil; Erich Widmer, Münchenstein; Reinhard Zell, Rodersdorf, all of Switzerland

[73] Assignee: Hoffmann-La Roche Inc., Nutley, N.J.

[21] Appl. No.: 40,625

[22] Filed: May 21, 1979

[30] Foreign Application Priority Data

Jun. 2, 1978 [CH] Switzerland .................. 6074/78
Mar. 29, 1979 [CH] Switzerland .................. 2922/79

[51] Int. Cl.³ .............................................. C07F 9/54
[52] U.S. Cl. ............................ 568/11; 260/340.5 R; 568/378
[58] Field of Search ................ 260/586 R; 568/378

[56] References Cited

U.S. PATENT DOCUMENTS

| 4,088,689 | 5/1978 | Rosenberger | 260/586 R |
| 4,098,827 | 7/1978 | Rosenberger | 260/586 R X |
| 4,111,992 | 9/1978 | Rosenberger | 260/586 R |
| 4,156,090 | 5/1979 | Kienzle | 560/61 |

OTHER PUBLICATIONS

Chem. Abstracts: 88:7127x; 88:170338a (Subject Index, vol. 88, 1978, p. 3733CS).

*Primary Examiner*—Ethel G. Love
*Attorney, Agent, or Firm*—Jon S. Saxe; George M. Gould; William H. Epstein

[57] ABSTRACT

The compound 6-hydroxy-3-(5-hydroxy-3-methyl-1,3-pentadienyl)-2,4,4-trimethyl-2-cyclohexen-1-one useful as intermediate for producing the natural coloring agent astaxanthin as well as a method for synthesizing astaxanthin from this compound and synthesizing the compound from 2-hydroxyketo isophorone.

2 Claims, No Drawings

PROCESS FOR THE MANUFACTURE OF CYCLOHEXENE DERIVATIVES

SUMMARY OF INVENTION

In accordance with this invention, it has been found that a compound of the formula:

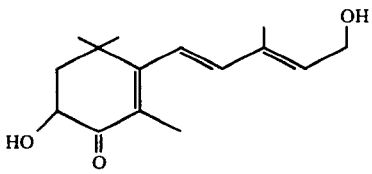

can be converted to astaxanthin by first halogenating the compound of formula I to produce a halide of the formula:

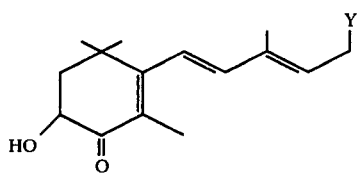

wherein Y is a halogen reacting the halide with a triaryl phosphine to produce a phosphonium salt of the formula:

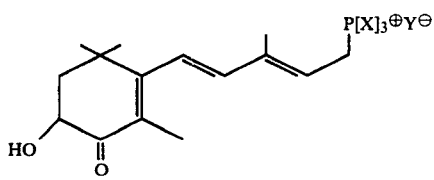

wherein X is aryl and Y is halogen which is condensed with a dialdehyde of the formula:

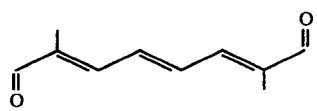

to produce either racemic or optically active astaxanthin.

In accordance with a further embodiment, the compound of formula I is produced from a 2-hydroxyketo isophorone of the formula:

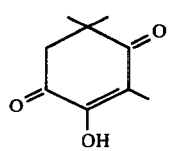

DETAILED DESCRIPTION OF THE INVENTION

As used above, the term halogen includes chlorine, bromine and iodine.

Also as used herein, the term aryl designates mononuclear or polynuclear or aromatic hydrocarbon groups which can be unsubstituted or substituted in one or more positions with a lower alkyl radical such as phenyl, naphthyl, anthryl, azulyl, tolyl, etc.

The term lower alkyl designates saturated aliphatic straight or branched chain hydrocarbon groups containing from 1 to 7 carbon atoms such as methyl, ethyl, n-propyl, isopropyl, n-butyl, etc. The term alkylene oxide designates alkylene oxides containing from 2 to 20 carbon atoms, preferably from 2 to 7 carbon atoms and having a single oxygen bridge. Among the preferred alkylene oxides are ethylene oxide, 1,2-butylene oxide and 1,2-propylene oxide.

In the foregoing formulae and in the following formulae the all-trans configuration is always shown. However, the invention also includes possible cis-configurations.

The halogenation of a diol of formula I can be carried out using a hydrogen halide (hydrogen chloride, hydrogen bromide or hydrogen iodide), i.e. in aqueous solution (e.g. 48% or 57%). The halogenation can be carried out at a temperature between about $-10°$ C. and $+10°$ C., preferably at about $0°$ C. As the solvent for the carrying out of the halogenation, there can be used a solvent which is suitable for such halogenations, for example a chlorinated hydrocarbon such as methylene chloride or chloroform. Any of the conditions conventionally utilized in halogenation with hydrogen halides can be utilized in carrying out this reaction.

The reaction of a thus-obtained halogenide with a triarylphosphine, especially with triphenylphosphine, to give a phosphonium salt of formula III can be carried out in a manner known per se; for example, in ethyl acetate, preferably in an inert atmosphere, and in the presence of an acid-binding agent (e.g. an alkylene oxide such as 1,2-butylene oxide), i.e. at about room temperature or at an elevated temperature.

The reaction of a resulting phosphonium salt of formula III with the dialdehyde of formula IV can likewise be carried out in a suitable solvent such as, for example, methylene chloride or chloroform and in the presence of an acid-binding agent such as 1,2-butylene oxide or a strong base such as sodium methylate.

The astaxanthin obtained in the foregoing manner is present, depending on whether a racemic or optically active starting material is used, in the form of the racemate [(3S,3'RS)-configuration] or in the optically active form [(3S,3'S)-configuration or (3R,3'R)-configuration] or in meso-form.

The present invention is also concerned with a process for the manufacture of certain intermediates, namely of cyclohexanone compounds, suitable for the aforementioned process for the manufacture of astaxanthin.

The process provided by the present invention for the manufacture of these cyclohexanone compounds comprises reducing 2-hydroxyketoisophorone of the formula

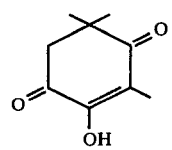

to give a diol of the formula:

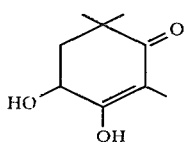 VI converting the free hydroxy groups in said diol of formula VI into protected hydroxy groups, optionally alkynylating and rearranging the product obtained to give the racemic or optically active acetylenediol of the formula

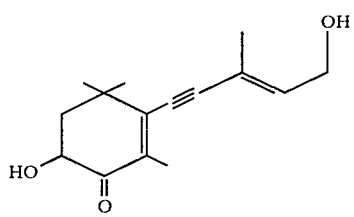 VII and optionally partially reducing said acetylenediol to give the diol of the formula

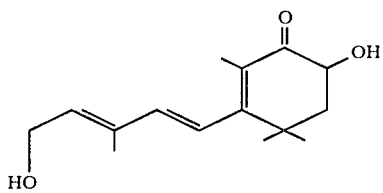 I

In the first step of this process, the 2-hydroxyketoisophorone of formula V is selectively reduced. This reduction is conveniently carried out by treating the 2-hydroxyketoisophorone of formula V in a suitable solvent, i.e. in aqueous-alkaline solution, with hydrogen in the presence of Raney-nickel. There is thus initially formed the alkali metal salt and this is subsequently reduced. This reduction can be carried out, for example, at room temperature.

The reduction product obtained is a tautomer mixture consisting of the diols of the formulae

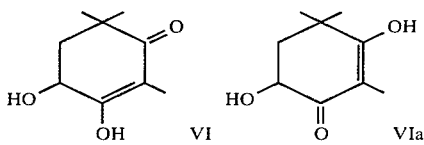

of which the diol of formula VI is the compound suitable for use in the next step of the process.

In order to block the desired tautomeric form in the diol of formula VI and to protect the two hydroxy groups contained therein, the hydroxy groups are converted into protected hydroxy groups. This is conveniently carried out by acetonization. This is accomplished by treating the mixture of the compound of formulae VI and VIa with an acetonizing agent, preferably acetone, to obtain a compound of the formula:

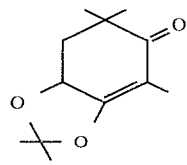 VIII in which the hydroxy groups present in the diol of formula VI are present in protected form.

The acetonization can, however, also be carried out using 2,2-dimethoxypropane or an isopropenyl alkyl ether such as isopropenyl methyl ether.

The acetonization can be carried out conveniently in a manner known per se under the conditions of an acid-catalysis and with the separation or removal of water from the reaction medium. Thereby, the diol of formula VIa present in the tautomer mixture from the preceding reduction is converted completely during the acetonization into the tautomer of formula VI and finally the entire material is fixed as the acetonide VIII.

The acetonization can be effected by reaction with acetone, the reactant acetone being used also as solvent. This acetonization is conveniently carried out at a temperature from room temperature to about 40° C. As acid catalyst there may be used e.g. perchloric acid or a Lewis acid, e.g. ferric chloride. The water can be removed from the reaction medium by any convenient method, e.g. by blowing an inert gas, such as nitrogen, through the reaction mixture and drying said gas, e.g. by means of a molecular sieve.

The protection of the hydroxy groups in the reduction product of formula VI can, however, also be carried out by dimerization of the diol of formula VI, i.e. conveniently by acid-catalysis with the separation or removal of water, for example by boiling with paratoluenesulfonic acid or perchloric acid in a suitable solvent (e.g. toluene). In this case the hydroxy groups present in the diol of formula VI are protected under intermolecular ether-formation and the formation of a dimer. A complete conversion of the tautomeric diol of formula VIa into the dimer also occurs in this case and at the same time the desired tautomeric form is fixed.

The next step of the process, namely the alkylation, is conveniently carried out under conditions in which a dehydration of the alkylation product and cleavage of the protecting group is brought about, i.e. under the conditions of an acid hydrolysis of the alkynylation product.

The alkynylation can be carried out using an optionally protected 3-methylpentenynol, for example with a silyl ether of 3-methylpentenyl-(1 or 3)-ol of the formula

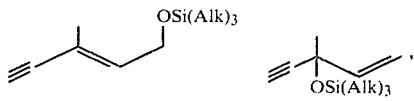

wherein Alk is lower alkyl, for example the methyl group, or with acetone 3-methy-2-penten-4-ynyl acetal or with tert.butyl 3-methyl-2-penten-4-ynyl ether, i.e. under conditions known per se for such alkynylations.

The alkynylation reaction is conveniently carried out in an inert solvent, such as tetrahydrofuran. The temperature at which the alkynylation reaction is per-formed lies preferably between about room temperature and about 40° C.

The acetylenediol of formula VII obtained after the alkynylation, dehydration and cleavage of the protecting groups is partially reduced in the next step to give the diol of formula I.

This partial reduction is conveniently carried out using zinc and glacial acetic acid.

As the solvent for the partial reduction there can be used a suitable organic solvent, for example a chlorinated hydrocarbon such as methylene chloride or, however, the glacial acetic acid used as the reagent.

There is preferably used a ca 2% solution of the acetylenediol in methylene chloride/glacial acetic acid, the latter being used approximately in the ratio of ca 1:2 to 1:2.5. The zinc is conveniently used in an amount of about 1–3 gram atoms, preferably 2.5 gram atoms, per mol of starting material.

The partial reduction can be carried out at a temperature between about −20° C. and about room temperature. The partial reduction is preferably carried out at about 0° C.

The resulting compound of formula I can then be converted into astaxanthin via a phosphonium salt of formula III in the manner described earlier.

In order to manufacture the optically active polyene compounds, the racemic diol of formula IV is resolved with a resolving base into the optically active forms and these optically active forms are subjected to the further steps of the process (VI→VIII→VII→I→III→astaxanthin).

As the resolving base there is conveniently used α-phenylethylamine, i.e. either (S)-(−)-α-phenylethylamine or (R)-(+)-α-phenylethylamine.

The optically acive compound of the formula

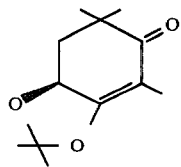

VIIIa required for the manufacture of natural astaxanthin occurring in salmon can, however, also be obtained by fermentatively reducing the compound of formula I with yeasts (e.g. with pressed yeast), there being obtained a mixture of the two tautomeric diols of formulae VI and VIa in the optically active form corresponding to the compound of formula VIIIa. This mixture is then acetonised in the manner described earlier in connection with the acetonisation of the mixture of diols of formula VI and VIa, there being obtained the optically active compound of formula VIIIa which is then converted via the corresponding optically active forms of formulae VII, I and III into the optically active natural astaxanthin occurring in salmon.

The following Examples further illustrate the present invention. Unless otherwise indicated, temperatures are in degrees Celsius and the ether is diethylether. All % are percentages by weight unless otherwise indicated.

EXAMPLE 1

A solution of 25 g of 6-hydroxy-3-(5-hydroxy-3-methyl-1,3-pentadienyl)-2,4,4-trimethyl-2-cyclohexen-1-one in 150 ml of methylene chloride is introduced into a 200 ml sulphonation flask provided with stirrer, 50 ml dropping funnel with pressure balance, thermometer and apparatus for inert gasification. The solution obtained is cooled to 0°–5° C. with an ice-bath under an argon atmosphere and subsequently held in this temperature range. 30 ml of hydrogen bromide solution (63% in water) are added dropwise as rapidly as possible while maintaining the temperature within the aforementioned range. The mixture is stirred for a further 5 minutes and then poured into 100 ml of 10 percent by sodium chloride solution in a 1 liter separating funnel. In addition, 400 ml of ethyl acetate are added to the separating funnel and then the mixture is shaken well. The aqueous phase, which is now at the bottom, is separated off and discarded. The organic phase is washed in two portions with a total of 200 ml of 5 percent sodium bicarbonate solution. The wash solutions are discarded. The organic phase is treated with 1 ml of 1,2-butylene oxide, dried over 50 g of anhydrous sodium sulphate, and filtered. The drying agent is rinsed on the filter with 100 ml of ethyl acetate and the bromide solution is subsequently concentrated to about 250 ml in a rotary evaporator under a water-jet vacuum at a bath temperature of 30° C. The partial vacuum in the rotary evaporator is maintained with nitrogen and the yellow concentrate obtained (containing 6-hydroxy-3-(5-hydroxy-3-methyl-1,3-pentadienyl)-2,4,4-trimethyl-2-cyclohexen-1-one) is used immediately for the preparation of the phosphonium salt.

A solution of 30 g of triphenylphosphine and 1 ml of 1,2-butylene oxide in 250 ml of ethyl acetate is introduced into a 1.5 liter sulphonation flask provided with stirrer, thermometer, 250 ml dropping funnel with pressure balance and apparatus for inert gasification. The vellel is gassed with argon during the entire duration of the reaction. The concentrated bromide solution prepared according to the preceding paragraph is now added dropwise at room temperature over a period of about 2 hours.

when the first signs of turbidity appear in the mixture seed crystals are added. The white phosphonium salt thereupon crystallizes out continuously and the temperature of the mixture rises slightly (up to about 28° C.). After the addition of the bromide has been completed, the mixture is stirred for a further 24 hours and then the product is filtered off under nitrogen. The white crystllizate is washed with 250 ml of ethyl acetate and then dried up to constant weight at 40° C. in a drying oven under a water-jet vacuum.

There are obtained 54.1 g of [(4E)-5-(4-hydroxy-2,6,6-trimethyl-3-oxo-1-cyclohexen-1-yl)-3-methyl-2,4-pentadienyl]-triphenylphosphonium bromide of melting point 172°–174° C.

69 g of the foregoing phosphonium bromide and 8.2 g of 2,7-dimethyl-octatriene-(2,4,6)-dial-(1,8) are dissolved in 250 ml of methylene chloride while stirring and gasing with argon in a 500 ml sulphonation flask provided with stirrer, 50 ml dropping funnel with pressure balance, thermometer and apparatus for inert gasification. This solution is cooled to 0°–5° C. with an ice-bath while stirring continuously and treated dropwise at this temperature over a period of 90 minutes with 27.6 ml of sodium methylate solution (containing 6.48 g of sodium methylate). 1 hour thereafter the cooling bath is removed and the mixture is left to react at room temperature for a further 18 hours.

After working-up with methylene chloride, isomerization by heating in heptane and further purification with methylene chloride and methanol, there are obtained 23.1 g of racemic astaxathtin of melting point 220°–222° C.

By working up with methylene chloride, it is meant that the reaction mixture is poured in an aqueous sodium bicarbonate solution, the resulting solution extracted with methylene chloride, the organic phase dried over anhydrous sodium sulfate, filtered and crystallized from methylene chloride and methanol.

40 g of sodium hydroxide are dissolved in 1.1 liters of water in a 3 liters hydrogenation apparatus provided with a stirrer and the solution, cooled to 20° C., is treated with 168.2 g of 2-hydroxy-3,5,5-trimethyl-2-cyclohexen-1,4-dione (2-hydroxyketoisophorone) and 28 g of Raney-nickel.

The air in the apparatus is now replaced by hydrogen and the reduction is started with vigorous stirring. After 4 hours or after uptake of about 25 liters of hydrogen, the hydrogen uptake comes to a standstill and, after a further hour, the catalyst is filtered off from the mixture and rinsed with water. The entire filtrate is acidified with 90 ml of 37% hydrochloric acid and partitioned between saturated sodium chloride solution and methylene chloride in separating funnels. The combined methylene chloride extracts are dried over sodium sulphate and evaporated up to constant weight in a rotary evaporator under a water-jet vacuum at a bath temperature of about 50° C. The residue, a mixture of the two tautomeric forms 3,4-dihydroxy-2,6,6-trimethyl-2-cyclohexen-1-one and 3,6-dihydroxy-2,4,4-trimethyl-2-cyclohexen-1-one, can be used directly in the following acetonization step.

For the acetonization, 200 g of the foregoing tautomer mixture in 1.5 liters of acetone are introduced into a drying tower provided with a stirrer and a water separator and packed with molecular sieves and treated dropwise while stirring at room temperature with 2 ml of 70 percent perchloric acid. After 6–7 hours at 30° C., 25 g of powdered anhydrous potassium carbonate are added to the orange colored solution.

The suspension is subsequently stirred at room temperature and while excluding moisture for 1 hour and then treated with 2 ml of pyridine. The solid materials are filtered off through a glass suction filter and washed on the filter with two 50 ml portions of acetone, i.e. with a total of 100 ml of acetone. The combined filtrates are evaporated in a rotary evaporator under a water-jet vacuum at a bath temperature of 30° C. The residue (a yellow oil) is treated with 600 ml of n-hexane and 100 ml of 1-N sodium carbonate solution, dissolved in the two pahses by vigorous shaking and the whole is subsequently partitioned in separating funnels between hexane and an aqueous phase consisting of 1-N sodium carbonate solution and saturated sodium chloride solution. The organic phases are combined, dried over sodium sulphate and concentrated to a ca 50% by weight solution in a rotary evaporator under a water-jet vacuum at a bath temperature of 40° C. The pale yellow solution is cooled to −30° C. in a 750 ml sulphonation flask (provided with stirrer, thermometer and calcium chloride tube) with an acetone/dry ice bath while stirring and left at this temperature for 5 hours. Upon cooling down the product begins to separate out in the form of heavy white crystals.

The crystals are filtered off under suction, washed on the filter with 150 ml of n-hexane (cooled to −35° C.) and subsequently dried up to constant weight at room temperature in a drying oven under a vacuum (0.2 mmHg). There are obtained 202 g of product of metling point 58°–59° C. From the mother liquor, there are obtained by distillation and crystallization of the distillate a further 29.6 g, so that the total yield of racemic 7,7a-dihydro-2,2,4,6,6-pentamethyl-1,3-benzodioxol-5(6H)-one amounts to 231.6 g.

60.8 g of magnesium turnings and 550 ml of absolute tetrahydrofuran are introduced into a 10 liter sulphonation flask provided with stirrer, thermometer, condenser with filled calcium chloride tube and 1 liter dropping funnel with pressure balance and argon gasification. A solution of 226 ml of ethyl bromide in 420 ml of absolute tetrahydrofuran is then dropwise within 50 minutes while stirring. After about 1 minute, the strong exothermic Grignard reaction spontaneously starts at room temperature. The velocity of the dropwise addition is adjusted so that the temperature can be maintained between 50°–60° C. with the aid of an ice-bath.

Subsequently, the mixture is heated with an oil-bath (bath temperature 80° C.) and stirred for 90 minutes.

Thereafter, the temperature of the mixture is adjusted to 40° C. while stirring continusously and then a solution of 500 ml of trimethyl-[(trans-3-methyl-pent-2-en-4-yn)-oxy]-silane (1″-pentol silyl ether) in 750 ml of absolute tetrahydrofuran is added dropwise over a period of 65 minutes.

While maintaining the described reaction conditions, the mixture is left for 2.5 hours and subsequently a solution of 210.3 g of the acetonide [racemic 7,7a-dihydro-2,2,4,6,6-pentamethyl-1,3-benzodioxol-5(6H)-one], prepared as described earlier, in 420 ml of absolute tetrahydrofuran is added dropwise over a period of 30 minutes.

The reaction conditions (stirring, 40° C., argon gasification) are maintained for a further 16 hours and then 500 ml of ether are added to the solution which has been cooled to room temperature.

The mixture is added to a mixture of 1000 g of crushed ice and 111 ml of 96 percent sulphuric acid and intensively stirred for 1 minute.

The aqueous phase is partitioned between ether and saturated sodium bicarbonate solution and saturated sodium chloride solution. The organic phases are combined, dried over sodium sulphate and evaporated up to constant weight in a rotary evaporator under a water-jet vacuum at a bath temperature of about 50° C. There are obtained 420 g of a crude product in the form of a brown oil which, after purification with isopropyl ether and hexane, gives 189 g of 6-hydroxy-3-(5-hydroxy-3-methyl-3-penten-1-ynyl)-2,4,4-trimethyl-2-cyclohexen-1-one in the form of light yellow crystals of melting point 84°–86° C.

In the next step, the thus-obtained ketodiol (150 g) in a 10 liter sulphonation flask (provided with stirrer, thermometer, calcium chloride tube and apparatus for inert gasification) is dissolved in 4.5 liters of methylene chloride and 0.975 liter of glacial acetic acid while stirring and gassing with argon. The solution is cooled to 0° C. and treated with 75 g of zinc dust.

While stirring continuously under argon at 0° C. there are added after 3 hours a further 25 g of zinc dust and, after a further 2 hours, the mixture is worked-up as follows.

The still cold mixture is filtered over a sintered glass filter and the residue is washed on the filter in two portions with a total of 600 ml of methylene chloride. The resulting methylene chloride extract is neutralized by washing with a saturated sodium bicarbonate solution and water. By drying over sodium sulphate, filtration and evaporation at 50° C. up to constant weight, there are obtained 158.7 g of a brown oil which, after purification with ether and hexane, gives 120.6 g of 6-hydroxy-3-(5-hydroxy-3-methyl-1,3-pentadienyl)-2,4,4-trimethyl-2-cyclohexen-1-one in the form of a cis/trans isomer mixture.

After crystallization from ether and evaporation of the mother liquor, there are obtained 83 g of the cis isomer in the form of yellow crystals of melting point 92°–94° C. and 35.9 g of a mixture of cis and trans isomers (1:1 parts by weight) in the form of a yellow oil.

The isomer mixture obtained after the reduction with zinc and glacial acetic acid can be subjected directly to halogenation and conversion into the phosphonium salt described earlier.

EXAMPLE 2

In a manner analogous to that described in Example 1, by reacting 10 g of 6-hydroxy-3-(5-hydroxy-3-methyl-1,3-pentadienyl)-2,4,4-trimethyl-2-cyclohexen-1-one with 16 ml of 37% by weight aqueous hydrochloric acid in 60 ml of methylene chloride in a 250 ml sulphonation flask there is obtained the corresponding chloride, this is reacted with triphenylphosphine to give [(4E)-5-(4-hydroxy-2,6,6-trimethyl-3-oxo-1-cyclohexen-1-yl)-3-methyl-2,4-pentadienyl]-triphenylphosphonium chloride (melting point 184°–186° C.) and the latter is reacted, also in a manner analogous to that described in Example 1, with 2,7-dimethyl-octatriene-(2,4,6)-dial-(1,8) to give racemic astaxanthin.

EXAMPLE 3

In a manner analogous to that described in Examples 1 and 2, racemic astaxanthin is obtained via [(4E)-5-(4-hydroxy-2,6,6-trimethyl-3-oxo-1-cyclohexen-1-yl)-3-methyl-2,4-pentadienyl]-triphenylphosphonium iodide (melting point 196°–198° C.).

EXAMPLE 4

In place of the silyl ether used in Example 1 for the alkynylation of 7,7a-dihydro-2,2,4,6,6-pentamethyl-1,3-benzodiozol-5(6H)-one there can also be used acetone methyl-3-methyl-2-penten-4-ynyl acetal (prepared for 1″-pentol and isopropenyl methyl ether).

EXAMPLE 5

The protection of the hydroxy groups in 3,4-dihydroxy-2,6,6-trimethyl-2-cyclohexen-1-one can also be carried out by dimerization as follows:

120 g of the tautomer mixture of formulae VI and VIa are dissolved in 1.4 liters of toluene and treated with 7 ml of 70% by weight perchloric acid in a 2 liter sulphonation flask equipped with stirrer, thermometer, water separator and apparatus for inert gasification.

While stirring and gassing with nitrogen, the mixture is boiled at reflux (water separator) for a period (about 5 hours) until starting material can no longer be detected by means of gas chromatographical analysis. While continuing the stirring and inert gasification, the mixture is cooled to room temperature and then made slightly alkaline with 12 ml of 28% by weight sodium hydroxide. The mixture is now flushed into a 3 liter separating funnel, washed in two portions with a total of 600 ml of water and finally evaporated up to constant weight in a rotary evaporator under a waterjet vacuum at a bath temperature of 60° C. The yellow-brown viscous residue is dissolved in 300 ml of acetone while warming and the solution in subsequently cooled to 0° C. with an ice-bath while stirring. The product thereby rapidly begins to crystallize. It is left to stand overnight in a refrigerator and then the crystallizate is filtered off under suction. The crystals are washed on the filter in two portions with a total of 50 ml of acetone (cooled to 0° C.) and subsequently dried up to constant weight in a drying oven under a water-jet vacuum at 50° C. The mother liquors are concentrated under reduced pressure at 50° C. and a further crop of crystals obtained therefrom by crystallization. There are obtained 83.8 g of the dimeric ether of the starting material in the form of crystals of melting point 206°–209° C.

This can be alkynylated with silyl ether and further processed in a manner analogous to that described in Example 1.

EXAMPLE 6

In order to manufacture the optically active polyene derivatives, especially the two optical antipodes of astaxanthin, the racemic 3,4-dihydroxy-2,6,6-trimethyl-2-cyclohexen-1-one is resolved according to the two following methods (a) and (b):

(a) 40 g of 3,4-dihydroxy-2,6,6-trimethyl-2-cyclohexene-1-one (in the form of the tautomer mixture obtained in accordance with example 1) are dissolved in 250 ml of absolute ether and 50 ml of absolute methanol. A solution of 28.7 g of (R)-(+)-1-phenylethylamine in 25 ml of absolute ether is added dropwise within 20 minutes while stirring. In so doing, an oil gradually separates out and the temperatures rises to 26° C.

The mixture is stirred for a further 16 hours. During this time, the separated oil disappears and a suspension of a yellow colored light powder forms. This is washed well with four 150 ml portions of absolute ether, whereby the initially sticky filter residue gradually becomes solid. The filter residue is dissolved in 400 ml of ethyl acetate at 70° C. in a rotary evaporator, seeded and then left overnight in a rotary evaporator with disconnected heating bath. The colorless crystallizate is filtered off and washed with three 100 ml portions of ethyl acetate. The filter residue is dried in a vacuum drying oven at 50° C. overnight. 14.57 g of the thus-obtained diastereomeric salt, dissolved in 100 ml of deionized water and 100 ml of methylene chloride, are introduced into a 500 ml separating funnel. After the addition of 20 ml of 3-N sulphuric acid, the mixture is vigorously agitated for 1 minute. The separated aqueous phase is back-extracted twice with 100 ml of methylene chloride each time. The combined methylene chloride phases are washed with 25 ml of saturated sodium chloride solution, dried over 20 g of sodium sulfate, filtered and the drying agent is rinsed on the filter twice with 50 ml of methylene chloride each time. The filtrate is evaporated up to constant weight in a rotary evaporator at a bath temperature of 40° C.

The thus-obtained (3S)-ketodiol can be further processed in a manner analogous to that described in Example 1 for the racemic ketodiol to give (3S,3′S)-astaxanthin (occurring in nature in salmon).

(b) 40 g of 3,4-dihydroxy-2,6,6-trimethyl-2-cyclohexen-1-one (in the form of the tautomer mixture obtained in accordance with Example 1) are dissolved in 250 ml of absolute ether and 50 ml of absolute methanol. The further processing is carried out in a manner analogous to that described in part (a) earlier and there is obtained the (3R)-ketodiol [[$\alpha$]$_D$ = +29.5 (1% in methanol)] which can be converted in a manner analogous to that described in Example 1 into (3R,3′R)-astaxanthin (occurring in nature in yeasts).

EXAMPLE 7

A fermentation broth consisting of 4.5 liters of deionized water, 500 g of pressed yeast, 250 g of sugar, 10 g of 2-hydroxy-3,5,5-trimethyl-2-cyclohexene-1,4-dione and 1 g of anti-foam agent (polypropyleneglycol monobutyl ether) is cultivated in a fermenter at 30° C. with surface aeration (240 liters/hour) and while stirring (900 revolutions/minute). 100 g portions of sugar are added after the fermentation has been carried out for 4 days and 5 days.

After carrying out the fermentation for 7 days, the fermentation broth is saturated with sodium chloride and extracted continuously with diethyl ether. After evaporating the ether, there is obtained a crude extract which contains the two tautomeric fermentation products, (−)-(S)-3,4-dihydroxy-2,6,6-trimethyl-2-cyclohexen-1-one and (−)-(S)-3,6-dihydroxy-2,4,4-trimethyl-2-cyclohexen-1-one.

By acetonization in a manner analogous to that described in Example 1, there is obtained (7aS)-7,7a-dihydro-2,2,4,6,6-pentamethyl-1,3-benzodioxol-5-(6H)-one, melting point 79°–80° C. [[α]$_D$= +105° (c=0.102% in dioxan)] which is converted into (3S,3′S)-astaxanthin in a manner analogous to that described in Example 1.

What is claimed is:
1. A phosphonium salt of the general formula

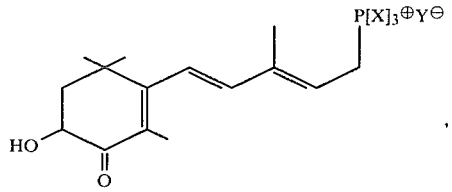

wherein X is aryl; and Y is halogen.
2. A phospnonium salt of claim 1 wherein X is phenyl.

* * * * *